United States Patent [19]

Olsson

[11] Patent Number: 5,713,831
[45] Date of Patent: Feb. 3, 1998

[54] METHOD AND APPARATUS FOR ARTERIAL REPERFUSION THROUGH NONINVASIVE ULTRASONIC ACTION

[76] Inventor: Sten Bertil Olsson, Norra Villavägen 23A, S-23734 Bjärred, Sweden

[21] Appl. No.: 284,639
[22] PCT Filed: Feb. 15, 1993
[86] PCT No.: PCT/SE93/00113
  § 371 Date: Sep. 16, 1994
  § 102(e) Date: Sep. 16, 1994
[87] PCT Pub. No.: WO93/15670
  PCT Pub. Date: Aug. 19, 1993

[30] Foreign Application Priority Data

Feb. 17, 1992 [SE] Sweden ............... 9200446

[51] Int. Cl.⁶ ............................................. A61B 17/22
[52] U.S. Cl. ................................... 601/2; 606/128
[58] Field of Search .................. 128/660.03, 661.01; 601/2-4; 606/128

[56] References Cited

U.S. PATENT DOCUMENTS

| | | | |
|---|---|---|---|
| 4,509,525 | 4/1985 | Seo | 128/661.01 |
| 5,178,135 | 1/1993 | Uchiyama et al. | 601/4 |
| 5,186,162 | 2/1993 | Talish et al. | 601/2 |
| 5,207,214 | 5/1993 | Romano | 601/4 |
| 5,269,291 | 12/1993 | Carter | 606/128 |
| 5,323,769 | 6/1994 | Bommannan et al. | 601/2 |

FOREIGN PATENT DOCUMENTS 0324948  7/1989  European Pat. Off. ............ 601/4

Primary Examiner—Ruth S. Smith
Attorney, Agent, or Firm—Ladas & Parry

[57] ABSTRACT

A method and apparatus for arterial reperfusion through non-invasive ultrasonic action transforms supplied energy into ultrasound signals and transmits the ultrasound signals into a body sufficiently to influence the dissolution of thrombus in a blood vessel in the body. A transducer for the transmitting has piezoelectric crystals, the crystals respectively sending the ultrasound signals each with a defined energy level and at least one frequency in an individual direction non-simultaneously with any other of the crystals.

19 Claims, 3 Drawing Sheets

METHOD AND APPARATUS FOR ARTERIAL REPERFUSION THROUGH NONINVASIVE ULTRASONIC ACTION

FIELD OF THE INVENTION

The present invention relates to an apparatus for subjecting the coronary arteries of the heart to ultrasound for the purpose of accelerating reperfusion.

Today infarct of the heart is a very common disease in the civilized world. In Sweden each year in the range of 35,000 individuals are stricken with acute infarct of the heart, a fourth of which dies even before they reach the hospital. The disease has a course with various types of complications in the acute stage, together yielding a death rate during the stay at the hospital in the range of nearly 15 percent, varying primarily with age and the magnitude of the infarct of the heart. After discharge from the hospital there is a clear excessive mortality, the more pronounced the larger heart muscle injury the patient has experienced because of his infarct. If it is possible to reduce the magnitude of the infarct of the heart in the acute infarct stage it has been found that this results in lower mortality in the postage of the infarct. The method having most evidently being able to reduce the heart muscle injury has been early reperfusion of the heart muscle by thrombolytic treatment. Hitherto the thrombolytic treatment has been in form of intravenous medication resulting in enzymatic dissolution of the formation of the thrombus in a coronary artery constituting the immediate cause of the acute infarct of the heart. The earlier the treatment has been able to be performed, the heifer effect has been achieved with respect to reducing the heart muscle injury and survival rate after the infarct.

STATE OF THE ART

With the purpose of noninvasively providing reperfusion as fast as possible, hitherto infarct of the heart has been treated with pharmaceuticals initiating enzymatic thrombolysis. Intravenous thrombolytic treatment of patients with accute infarct of the heart results in reperfusion after 30–150 minutes, on the average after approximately 45 minutes. The potential gain in being able to reperfuse the myocardium immediately instead of having to wait 45 minutes is obvious. The possibility of accelerating thrombolysis under experimental conditions by subjecting the thrombus to ultrasound has been shown by the applicant. The present invention substantially reduces the time to reperfusion in that this experimentally confirmed principle using the claimed apparatus may be applied on patients having a suspected acute infarct of the heart.

A known apparatus closely related to the present invention is a diagnostic apparatus using ultrasound. The apparatus comprises an ultrasound transmitter and a receiver receiving the echo from the ultrasound when this is reflected against various organs of the body. The sound energy emitted is so low that no effect on the organ can be found.

Ultrasound apparatus may also be used for heating organs of the body, e.g. joints and muscles, for therapeutic reasons. In this case higher energy levels are used than in the present invention.

Another apparatus related to the present invention is renal calculus crushers, which are used to fragmentize renal calculi without surgical operation. The supplied energy, which may be sound energy, is focused such than the power is highly concentrated to the renal calculus itself, which in contrast to a thrombus is easily located using diagnostic ultrasound or X-rays. The difference in hardness between the renal calculus and the surrounding organs promotes the transmission of the destructive energy to the renal calculus.

SUMMARY OF THE INVENTION

The present invention provides a method and apparatus for reperfusion through accelerated thrombolysis. The method and apparatus utilizes ultrasound to influence a thrombus formed in a blood vessel. By means of the invention reperfusion may be obtained quicker than through enzymatic treatment only. The exact mechanism underlying the desired effect is not completely mapped out but it is believed to be some or more of the known physical effects provided by ultrasound energy in the present form.

According to the invention the apparatus comprises an energy supply, a control controlling the amount and characteristics of the supplied energy and a compound ultrasound transmitter, i.e. transducer for transforming the energy to sound energy and subjecting the entire coronary artery tree to ultrasound. Thus, it is not necessary to know the exact location of the thrombus.

In order to be able to distribute the desired energy of the sound signal to the entire coronary artery tree, the transmitter utilizes various sound emitting crystals emitting sound of various wavelengths, of various beam directions and variously shaped beam sectors. Sound signals are transmitted intermittently from the individual crystals.

Embodiments of the invention are set forth more in detail in the accompanying claims.

BRIEF DESCRIPTIONS OF THE DRAWINGS

The invention will now be described in detail referring to the enclosed drawings of which:

DETAILED DESCRIPTION OF THE PREFERRED EMBODIMENTS OF THE INVENTION

Figure 1:
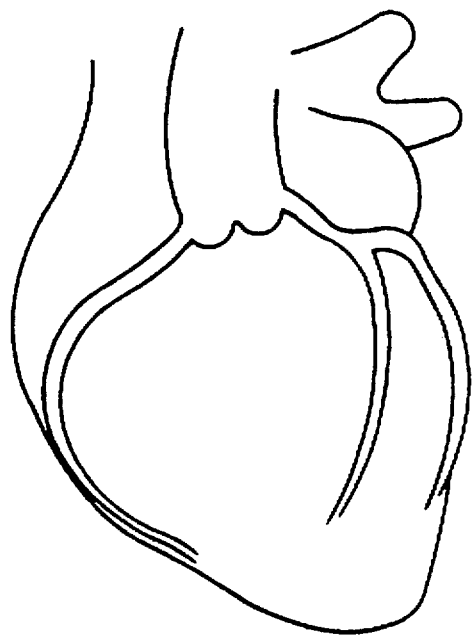
FIG. 1 is a simplified view of the heart seen from the front.

It is now totally accepted that most of the infarcts of the heart are caused by thrombus formation in the coronary arteries of which a few are shown in FIG. 1. These thrombi are derived from an injury of the cells lining the vessel, an endothelial injury. This is caused in turn, partly, by structural vessel transformations caused by a slow atheromatous process. Thrombocytes are aggregated at the injured endothelian surface, whereby a thrombycyte agglutination is formed, complexed by fibrin precipitation and further built-up by coagulation. The obliterative process may also contain components of vascular spasms.

The initial thrombus consists of a fragile tissue mass, but as fibrin is precipitated succesively the thrombus is even after a few hours more mecanically resistant. The fragile thrombus is a known phenomenon to everybody who has suffered from nosebleed. When this has been stopped it is important not to mechanically irritate the vessel region in which the nosebleed started. A similar influence of a fragile throumbus in a coronary artery in acute infarct of the heart results in the thrombus being fragmentized, embolized and reperfusion is achieved.

The present invention provides an apparatus by means of ultrasound transmitting energy from the exterior of the body to the blood vessel containing an obliterative thrombus. By applying sound waves transthoracically and/or via an esophageal probe a quick action on the thrombus may be achieved.

Figure 2:
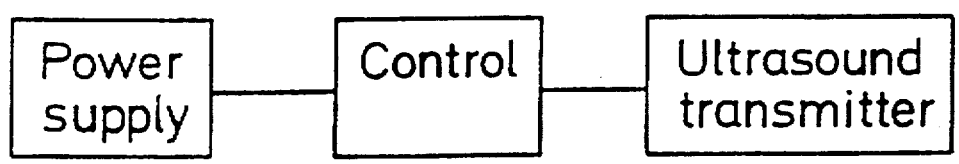
FIG. 2 is a block diagram of the components included in the device.

FIG. 2 shows schematically the structure of the apparatus according to the invention. It comprises a power supply supplying electrical energy, a control for controlling the power supply to a compound ultrasound transmitter, in turn transforming the energy to sound energy which is distributed so that the whole tissue volume, within which the thrombus is thought to exist, is subjected to sound energy of the necessary level.

The transmitter is composed of several transmitting units, each comprising at least one piezoelectric crystal. The transmitting units are applied directly against the chest of the patient and/or, is in an esophageal probe, inserted in the esophagus directly behind the heart.

Figure 3:
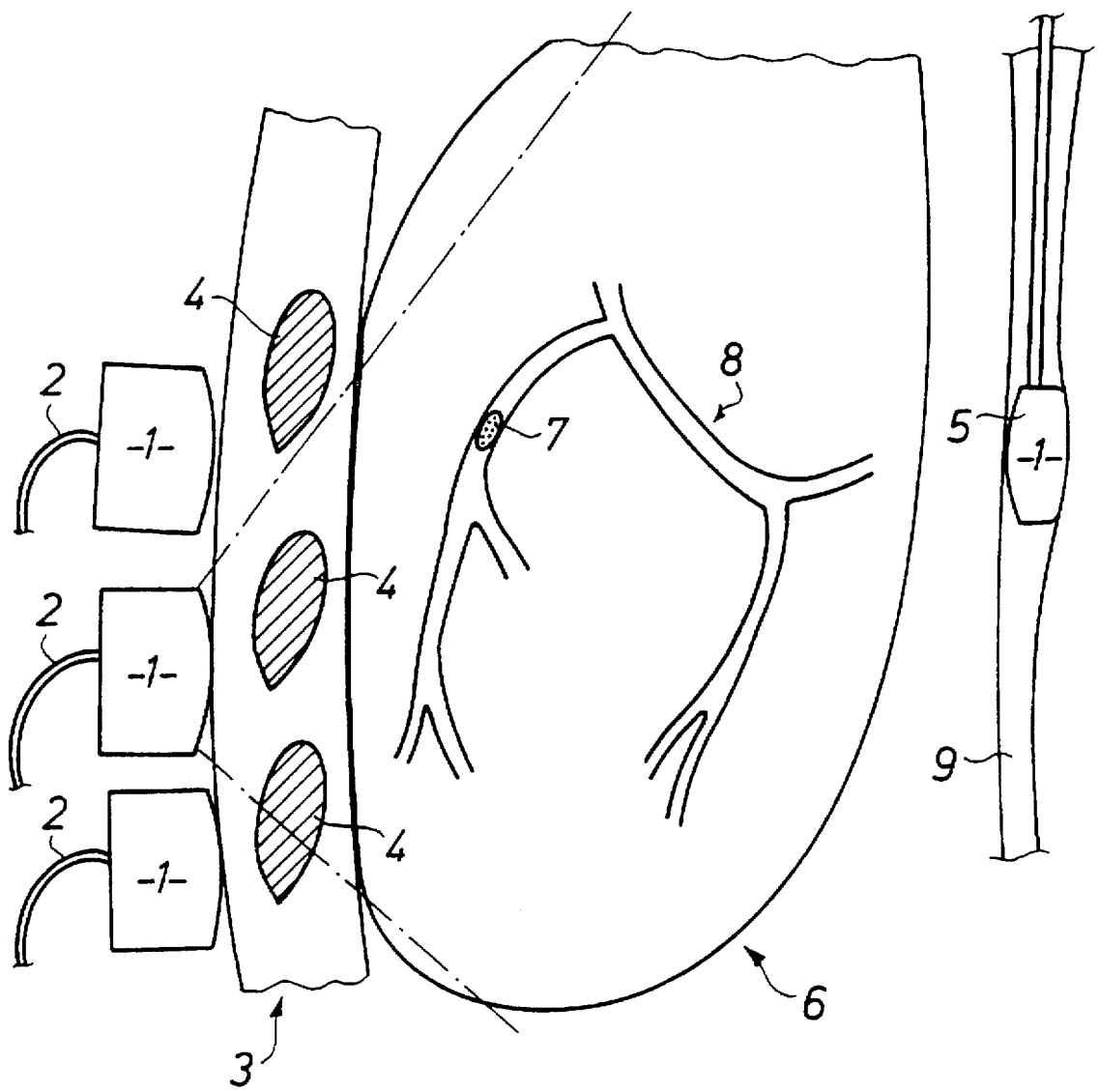
FIG. 3 is a schematic view of the ultrasound transmitter according to the the invention.

FIG. 3 shows an embodiment of the apparatus used to influence a thrombus in the heart of a human. The ultrasound transmitter consists of several transmitting crystals 1 connected by wires 2 to the control. Three crystals are applied against the chest 3 of the patient shown in cross-section with three ribs 4 visible and one crystal is located in an esophageal probe 5. The esophagus 9 passes close to the rear of the heart enabling irradiation of the heart 6 at this side without the need to raise the power unnecessarily at the front. Each crystal transmits ultrasound in a sector independent of the others. The sectors are directed such that the largest possible part of the heart 6 is subjected to the ultrasound, since it is not known exactly where the thrombus is located. In the figure the thrombus is shown at 7 in a coronary artery 8.

The control controls the transmitter to transmit signals from the various individual crystals in the compound ultrasound transmitter. Because each separate crystal transmits an ultrasound signal of a defined energy level and with defined time intervals and in individual directions as well as different impulse propagation of the signal, complete action on the treated organ is achieved. The various crystals are controlled such that they transmit pulses one at a time, i.e. they never transmit simultaneously.

Figure 4:
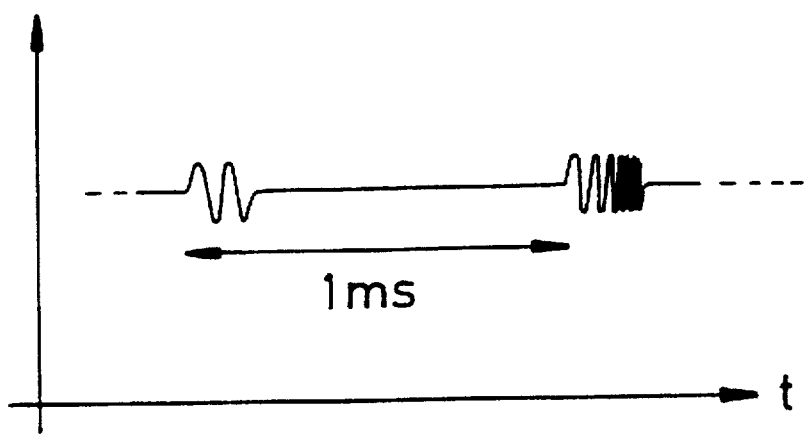
FIG. 4 is a diagram of possible pulse shapes.

The transmitter supplies sound energy in pulses having a pulse frequency which can be varied. FIG. 4 shows a diagram of possible pulse shapes. The pulse frequency may be varied within broad limits, e.g. from 10 Hz to 10 kHz. A pulse frequency of 1 kHz, as calculated for the entire compound transmitter, has yielded good results. The interval between the pulses is then 1 ms, as is shown in FIG. 4. The duration of the pulses may be varied in turn between 1 μs and 50 μs and 10 μs seems to be a suitable value. During the pulses the output power of the transmitter is e.g. 2 W/cm², maximum 3 W/cm². During the silent periods diagnosis may be performed with the transmitter or with a separate transmitter for ultrasound diagnosis (see below).

The sound frequency is suitably in the range of 25 kHz–5 MHz. The sound frequency may be fixed, as illustrated in the left pulse. However, it may be more advantageous to let the sound frequency sweep over a range, e.g. 25 kHz–5 MHz.

Figure 5:
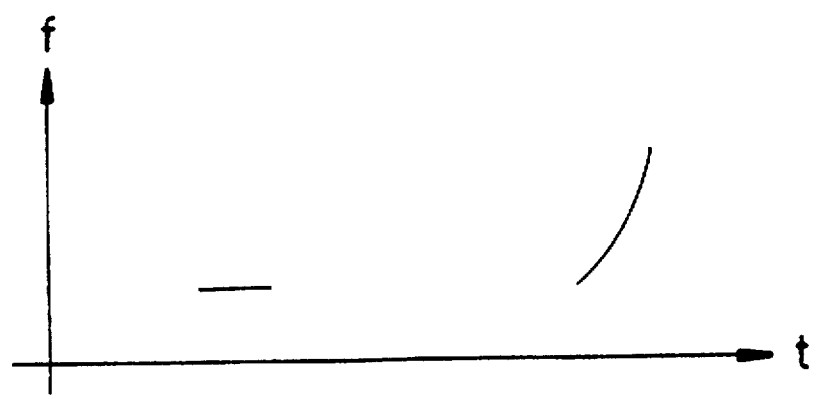
FIG. 5 is a diagram of the frequency of the pulses of FIG. 4.

FIG. 5 illustrates schematically the sound frequencies of the pulses in FIG. 4. The frequency sweep may be linear or along a suitable curve. The shape of the sweep is net critical.

A person having acute infarct of the heart caused by a thrombus in the coronary arteries has most often a severe, acute felt pain in the chest, agony and seeks, provided he can, generally medical help as soon as possible. The enzymatic treatment of the thrombus is started immediately by intravenous treatment with medicine, provided contraindications to such treatment are not present. The treatment with the apparatus according to the invention is likewise started as soon as possible. Since it is not known exactly where in the coronary artery the thrombus is present, a sound signal is transmitted passing the whole heart.

In an embodiment the apparatus of the invention may be integrated with an ultrasound diagnosis apparatus. One optional transmitting unit is used for the diagnosis. It will then be possible to study simultaneously the effects of the treatment. Thanks to the pulsed sound shape intervals between the therapeutical sound pulses may be used for the diagnostic ultrasound.

In connection with therapeutic treatment with ultrasound of joints and muscles and in connection with treatment of renal calculus, the effects of ultrasound on the tissues of the body has been studied. It has been found that the heart is remarkably resistant to possible trauma which may occur. Thus, there is a very little risk that the treatment with the apparatus of the invention will cause any adverse effects in the heart. This possible effect should in that case be compared to the effect of the infarct itself, which of course can be lethal.

Is is appreciated that the apparatus of the invention also can be used for treatment of thrombi located in various types of vessels in various other organs than the heart, e.g. thrombi in the legs. The invention is only limited by the claims below.

I claim:

1. In an apparatus for arterial reperfusion through noninvasive ultrasonic action comprising supply means for supplying energy and an ultrasound transducer means for transforming the supplied energy into ultrasound signals and transmitting the ultrasound signals into a body in an amount effective to influence the dissolution of thrombus in a blood vessel in the body, the improvement wherein the transducer means has transmitting units respectively comprising piezoelectric crystals, the crystals respectively sending the ultrasound signals each with a defined energy level and at least one frequency in an individual direction at a non-overlapping time with respect to any other of the crystals.

2. Apparatus according to claim 1, wherein the transducer means transmits the sound energy in pulses at a pulse frequency.

3. Apparatus according to claim 2, wherein the ultrasound signals have an output power from the supplied energy, the output power being up to 3 W/cm².

4. Apparatus according to claim 2, wherein the pulse frequency is in the range of 10 Hz–10 kHz.

5. Apparatus according to claim 4, wherein each of the pulses has a duration in the range of 1 μs–50 μs.

6. Apparatus according to claim 5, wherein the duration is approximately 10 μs.

7. Apparatus according to claim 4, wherein the pulse frequency is approximately 1 kHz.

8. Apparatus according to claim 2, wherein the frequency is in the range of 25 kHz–5 MHz.

9. Apparatus according to claim 8, wherein the transducer sweeps the frequency within each of the pulses from 25 kHz to 5 MHZ.

10. Apparatus according to claim 1, wherein the frequency is in the range of 25 kHz–5 MHz.

11. Apparatus according to claim 1, and further comprising an esophageal wherein at least one of the transmitting units is in the esophageal probe.

12. A method for arterial reperfusion through noninvasive ultrasonic action, comprising: supplying energy;

and transforming the supplied energy into ultrasonic sound energy into ultrasonic sound energy and non-overlappingly transmitting the ultrasonic sound energy from any of individually directed crystal transmitting units into a body for influencing the dissolution of thrombus in a blood vessel in the body.

13. Method according to claim 12, wherein the sound energy is in pulses having a pulse frequency.

14. Method according to claim 13, wherein the sound energy has an output power up to 3 W/cm$^2$.

15. Method according to claim 14, wherein the pulse frequency is in a range of 10 Hz–10 kHz.

16. Method according to claim 15, wherein each of the pulses has a duration in the range of 1 µs–50 µs.

17. Method according to claim 16, wherein the ultrasonic sound energy has at least one sound frequency in the range of 25 kHz–5 MHz.

18. Method according to claim 17, wherein the sound frequency sweeps within each of the pulses from 25 kHz–5 MHz.

19. Method according to claim 18, wherein the transmitting is from outside of the body.

* * * * *